United States Patent [19]

Suzuki

[11] Patent Number: 4,781,459
[45] Date of Patent: Nov. 1, 1988

[54] APPARATUS FOR MEASURING THE AMOUNT OF MINUTE PARTICLES CONTAINED IN LIQUID

[75] Inventor: Riichiro Suzuki, Kyoto, Japan
[73] Assignee: Horiba, Ltd., Tokyo, Japan
[21] Appl. No.: 854,760
[22] Filed: Apr. 22, 1986
[30] Foreign Application Priority Data

May 17, 1985 [JP] Japan .............................. 60-74127[U]

[51] Int. Cl.$^4$ ............................................ G01R 15/02
[52] U.S. Cl. ...................................... 356/335; 356/73; 356/339
[58] Field of Search ............................... 356/335–339, 356/73

[56] References Cited

U.S. PATENT DOCUMENTS

| | | | |
|---|---|---|---|
| 3,661,460 | 5/1972 | Elkins et al. | 356/335 |
| 3,826,364 | 7/1974 | Bonner et al. | 356/13 |
| 3,861,198 | 1/1975 | Shea | 73/61 R |
| 3,989,381 | 11/1976 | Fulwyler | 356/338 |
| 4,273,318 | 1/1981 | Stöhr | 356/73 |
| 4,515,274 | 5/1985 | Mollinger et al. | 356/73 |
| 4,683,212 | 7/1987 | Uffenheimer | 436/52 |

FOREIGN PATENT DOCUMENTS 58-6448  1/1983  Japan .

Primary Examiner—R. A. Rosenberger
Assistant Examiner—Crystal Cooper
Attorney, Agent, or Firm—Wenderoth, Lind and Ponack

[57] ABSTRACT

An apparatus for measuring particles contained in a sample liquid has a cylindrical cell having an incident light transmitting portion, a transmitted light transmitting portion diametrically aligned with the incident light transmitting portion, and a light transmitting portion at an angle to the diameter between the incident light transmitting portion and the transmitted light transmitting portion. An inlet at one end of the cell admits sheath flow liquid having the same index of refraction as the sample liquid, and an outlet is provided at the other end of the cell. A rectifying cylinder is positioned within said cell and has the axis extending between the inlet and the outlet and perpendicular to the diameter between the incident light transmitting portion and the transmitted light transmitting portion and having light passing holes therein aligned with the incident light transmitting portion, the transmitted light transmitting portion and the scattered light transmitting portion, the cylinder causing sheath flow liquid to flow smoothly from the inlet to the outlet at a predetermined pressure thereof and directed toward said outlet and upstream of the diameter and discharges sample liquid into the cylinder at a pressure higher than the predetermined pressure. An optical detector optically connected to the scattered light transmitting portion detects light scattered from particles in the sample liquid.

4 Claims, 6 Drawing Sheets

APPARATUS FOR MEASURING THE AMOUNT OF MINUTE PARTICLES CONTAINED IN LIQUID

BACKGROUND OF THE INVENTION

1. Field of the Invention

The present invention relates to an apparatus for measuring the amount of minute particles contained in pure water and other liquids used for washing and the like during a process for manufacturing integrated circuits.

2. Description of the Prior Art

Superpure water containing a very small amount of minute particles has been used for washing and the like in a process of manufacturing integrated circuits. A measuring apparatus as shown in FIG. 6 has been used as a measuring apparatus for measuring the amount of minute particles contained in liquids used as washing water in such process.

Referring now to FIG. 6, the apparatus has a parabolic reflecting mirror 61, an optical detector 62 provided at the focal point of said reflecting mirror 61 opposite said reflecting mirror 61 and to which all light emanating from an origin O is reflected, source of light 63, such as a tungsten lamp, arranged behind said reflecting mirror 61, a beam of light being incident upon said origin O of said reflecting mirror 61 through an optical system 64 and a passing-through hole 65 formed in said reflecting mirror 61. A glass tube extends through the origin O of said reflecting mirror 61 at right angles to said incident beam, said glass tube 66 being supplied with water the particle content of which is to be measured. A trap 67 is disposed between said glass tube 66 and said detector 62 for preventing the beam of light from said source of light 63 from reaching the detector 62 directly.

In the measurement of the amount of particles by this apparatus, a beam of light from the source of light 63 is irradiated on water, the particle content of which is to be measured, in the glass tube 66, and scattered light scattered by a particle is reflected by the reflecting mirror 61 to the detector 62, and the input to the detector being a measure of the number of particles contained in a unit volume of water.

With the above described conventional apparatus, since the beam of light is irradiated on water passing through the glass tube 66 and the number of particles is counted, some scattered light is produced in the glass tube 66 due to a difference between the refractive index of the glass in the tube 66 and that of the water, and this reaches the detector 62 as noise, and causes the S/N ratio to be bad. A problem also occurs that if the scattered light from the particles is weak, it is difficult to be detected apart from the scattered light from the glass tube 66, whereby the lower limit of the size of detectable particles is about 0.5 μm, and the detecting accuracy is also low.

SUMMARY OF THE INVENTION

The present invention has been made in order to solve the above described problems and seeks to provide an apparatus for measuring the amount of particles contained in a liquid which eliminates the scattered light produced at the interface of a liquid to be measured and the container, and detects the amount of particles with a high degree of accuracy.

The apparatus for measuring the amount of minute particles contained in a liquid according to the present invention comprises a cylindrical cell provided with a transmitting portion for incident light, a transmitting portion for light scattered by the collision of the incident light with particles within the sample liquid, an inlet for a sheath flow liquid and an outlet for the liquids; a rectifying cylinder in the cell provided with a transmitting hole for the incident light, and for light transmitted through the cylinder, and one for light scattered by particles to be detected; a nozzle directed coaxially into said rectifying cylinder for discharging the sample liquid at a pressure higher than that of the sheath liquid; partition wall on the outside of the rectifying cylinder between the transmitting hole for the incident light and the transmitting hole for light from the particles to be detected; and an optical detector for detecting the light from the particles to be detected.

With the apparatus according to the present invention, a sheath liquid having the same index of refraction as the sample liquid and put in a cell through an inlet thereof passes through the cell and the rectifying cylinder and simultaneously the sample liquid is discharged into the sheath flow liquid through a nozzle at a pressure higher than that of the sheath flow liquid thereby causing the sample liquid to flow in a laminar flow surrounded by the sheath liquid due to the difference in pressure between them. Incident light, which passes through a transmitting portion of the cell and a transmitting hole of a rectifying cylinder, is directed onto said laminar flow of sample liquid and scattered light produced by the collision of the incident high with particles contained in the sample liquid is detected by the optical detector, thereby measuring the number of particles contained in the liquid to be measured. Since there is no difference between the refractive index of the sheath liquid and that of the sample liquid, no scattered light is produced at an interface between them, whereby a measurement of high accuracy can be achieved.

DESCRIPTION OF THE PREFERRED EMBODIMENT

Figure 1:
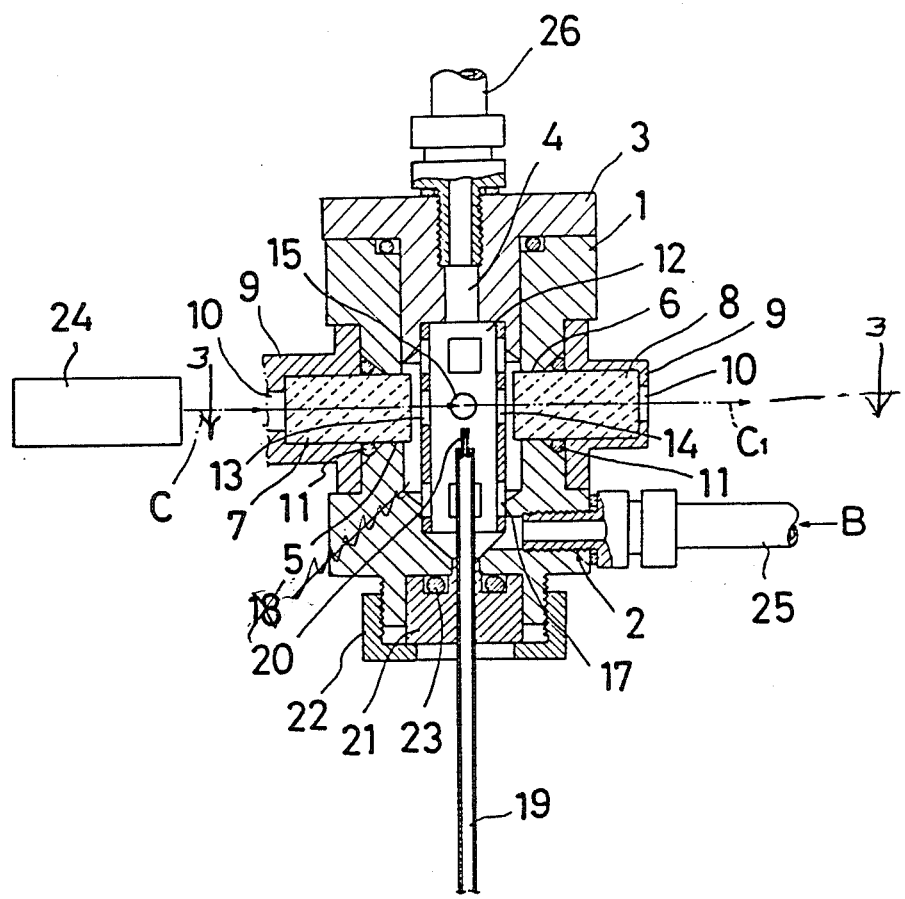
FIG. 1 is a longitudinal sectional view showing one embodiment of an apparatus for measuring the amount of minute particles contained in a liquid according to the present invention.

Referring now to FIG. 1, a cylindrical cell 1 is provided which is formed of metal such as aluminum or formed of opaque synthetic resin and which has an inlet 2 in a circumferential wall at one end thereof through which a sheath flow liquid B is caused to flow, and a cap 3 at the other end thereof, said cap 3 being provided with an outlet 4 for allowing said sheath liquid to flow out of the cell 1.

Window holes 5 and 6 are provided in the circumferential wall of the cell 1 at substantially diametrically opposite positions for transmitting portions of incident light into the cell 1, and transmitting bodies or cell windows 7 and 8 are mounted said window holes 5 and 6 for closing the window holes 5 and 6. Said transmitting bodies 7 and 8 are formed of transmitting substances such as silica glass in a columnar shape and blackened with paint or the like on the periphery thereof. Cap-like fitting members 9 are fitted over the outer ends of bodies 7 and 8 and have flanges thereon mounted in recesses in cell 1 for fixedly mounting the transmitting bodies 7 and 8 on the cell 1, and are each provided with an opening 10 in the end covering the bodies 7 and 8. O-ring 11 is provided around each body 7 and 8 sealing it in the cell 1.

A rectifying cylinder 12 is positioned substantially coaxially in the cell 1 with a circumferential space between it and the internal surface of the cell 1 communicating with the inlet 2 and the outlet 4. Although this rectifying cylinder 12 can be formed of any one of a number of materials, etc., opaque synthetic resins such as ABS resin, rubber or aluminum which has been subjected to a black-alumite treatment, it is preferably colored black or the like so as to reduce the reflection of light therefrom.

Figure 3:
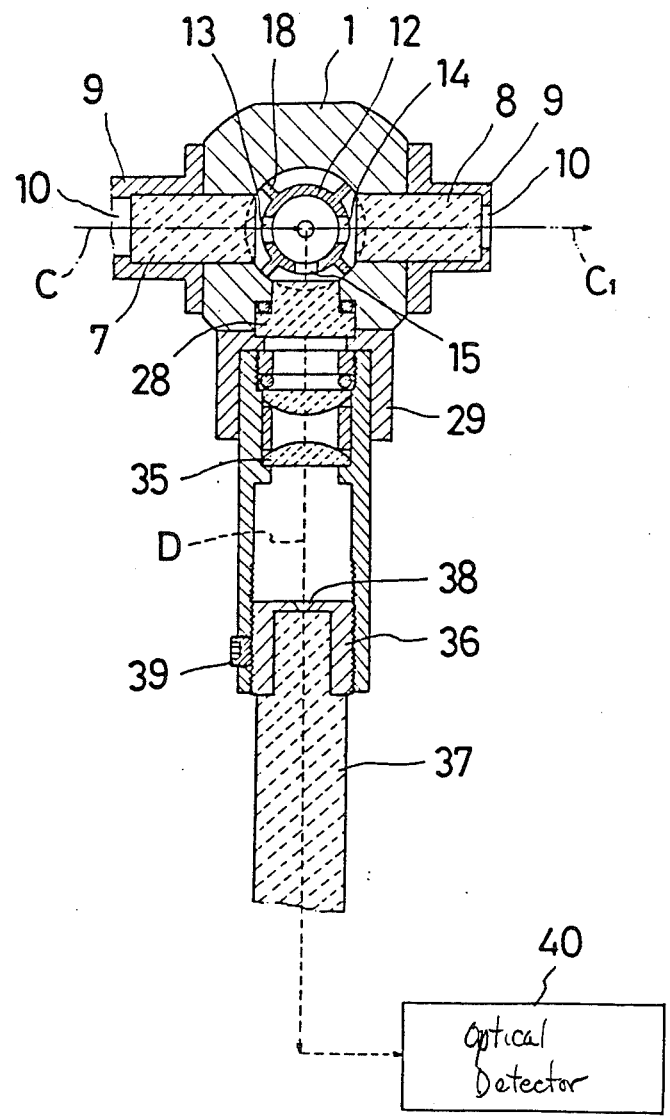
FIG. 3 a transverse sectional view taken along line 3—3 of FIG. 1.

Openings 13 and 14 are formed in the rectifying cylinder 12 aligned with the light transmitting bodies and the rectifying cylinder 12 is provided with an opening 15 for passing a beam of detecting light therethrough at a position meeting at almost right angles with an axis through the openings 13 and 14. A plurality of liquid-passage holes 17 are provided in the rectifying cylinder 12 for flowing the sheath liquid in and around the rectifying cylinder 12, and partition walls 18 are provided on the periphery of the rectifying cylinder 12 and extending in the axial direction of the rectifying cylinder 12 between the opening 13 and the opening 15 as well as between the opening 14 and the opening 15 (refer to FIG. 3).

A pipe 19 for supplying sample liquid extends through the bottom of the cell 1 adjacent the inlet 2 into the rectifying cylinder 12 and is provided with a nozzle 20 mounted on the inner end thereof. The nozzle 20 approaches the opening 13 but does not overlap the opening 13. A supporting block 21 for the supply pipe 19 is mounted on the cell 1 by means of a cap nut 22 and is sealed thereagainst by an O-ring 23.

A source of light 24 directs a beam of light C into the rectifying cylinder 12 through the transmitting body 7. A sheath liquid supply pipe 25 is connected to the inlet 2 and a drainage pipe 26 is connected to the outlet 4.

Figure 2:
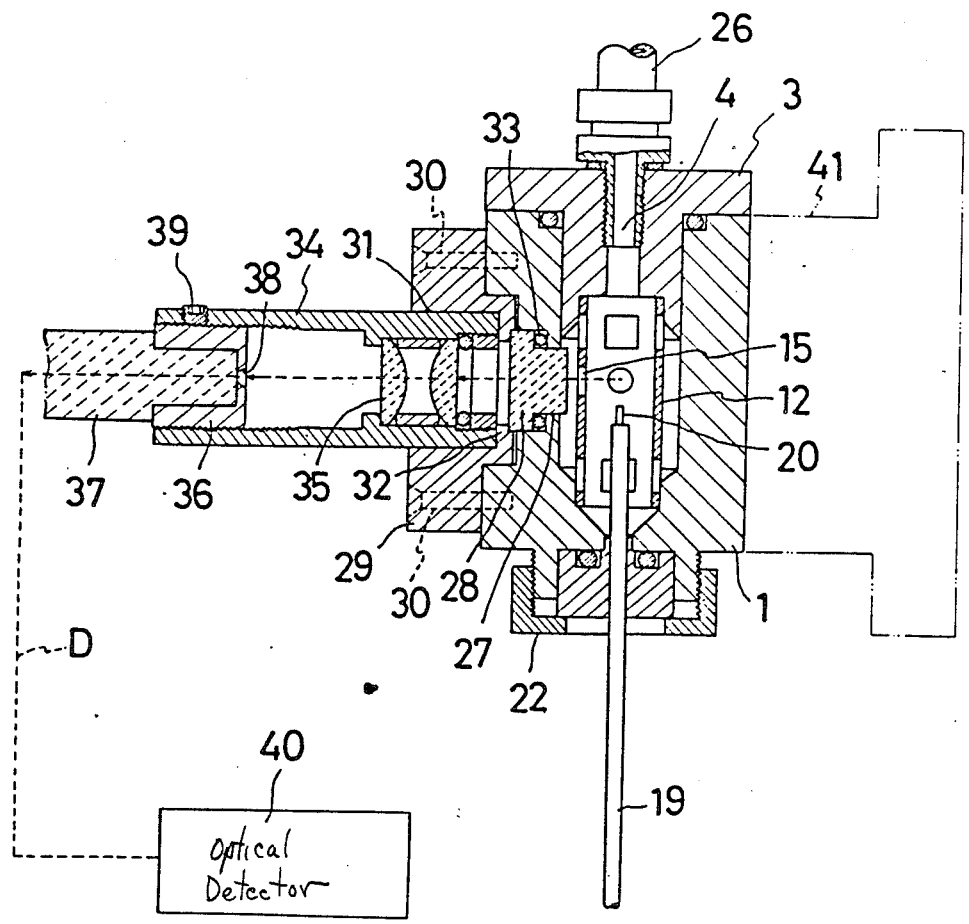
FIG. 2 is a longitudinal sectional view of the apparatus of FIG. 1 taken along a plane rotated 90° around the longitudinal axis thereof from the plane of the view in FIG. 1.

As shown in FIG. 2, hole 27 is provided in the cell 1 opposite the opening 15 for passing the beam of detecting light therethrough and has a transmitting body 28 therein formed of a transmitting substance such as silica glass, said transmitting body 28 having one end projecting into the cell 1. The peripheral surface of this transmitting body 28 is covered with black paint or the like similar to said transmitting bodies 7 and 8. A fitting block 29 is fixedly mounted on the cell 1 by means of setscrews 30 and has a stop step 32 pressing said transmitting body 28 into an O-ring 33 on a seat around hole 27, and has a receiving hole 31 therein.

A support cylinder 34 has one end mounted in the receiving hole 31 and has an optical system 35 inside said one end thereof in opposed relation to the transmitting body 28. A transparent sleeve 36 having a closed end is adjustably mounted inside the other end of the support cylinder and is held in position by means of a set screw 39. One end of an optical fiber 37 is fixedly held in sleeve 36 and a pin hole 38 is provided in the closed end opposed to the optical system 35. An optical detector 40 is connected to the other end of the optical fiber 37. The cell 1 is in turn supported by a cell supporting block 41 shown in phantom lines in FIG. 2.

Figure 4:
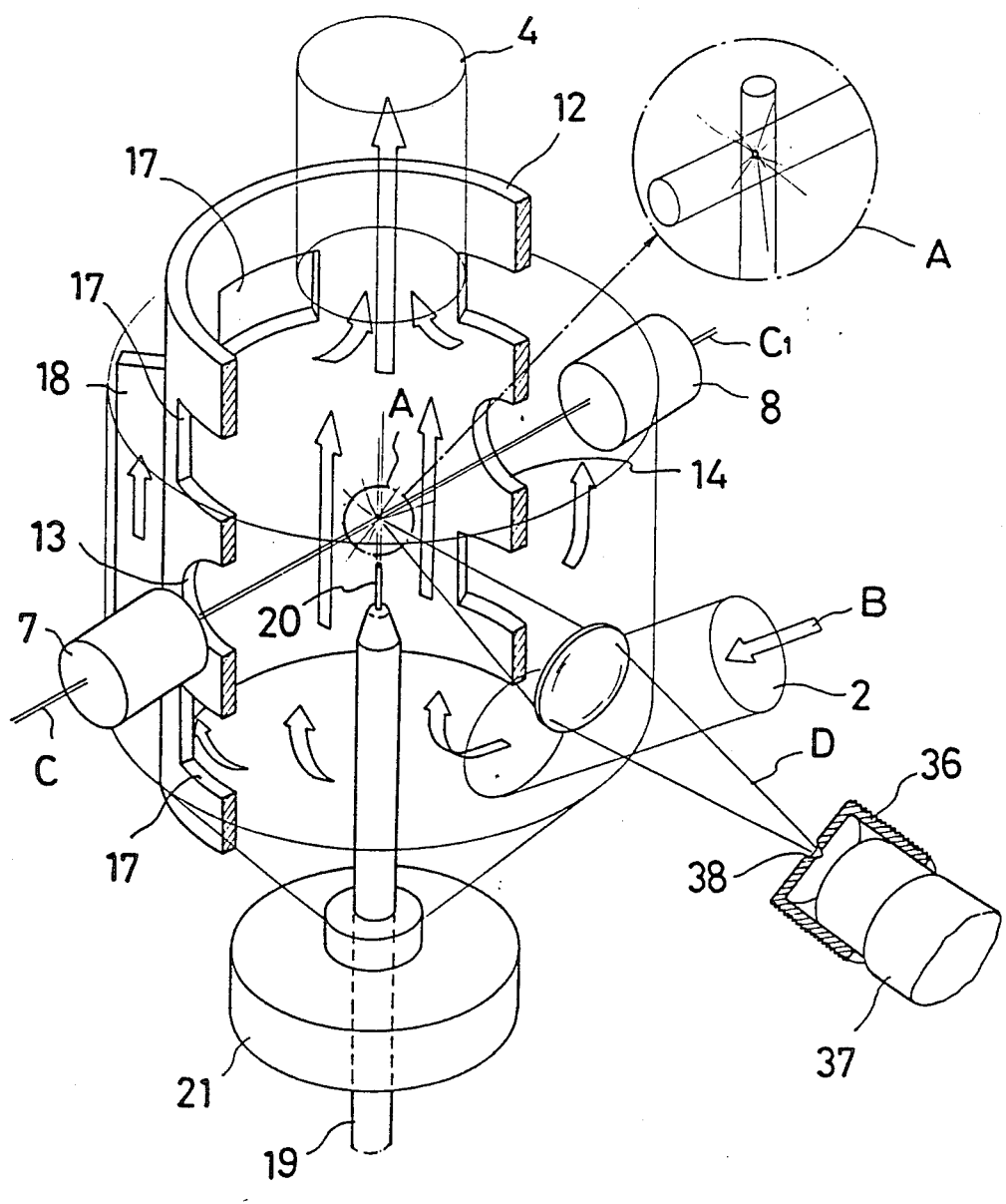
FIG. 4 is a perspective view of the apparatus of FIG. 1 showing a rectifying cylinder partly in section and in which a fitting member is slightly separated from an optical fiber.
Figure 5:
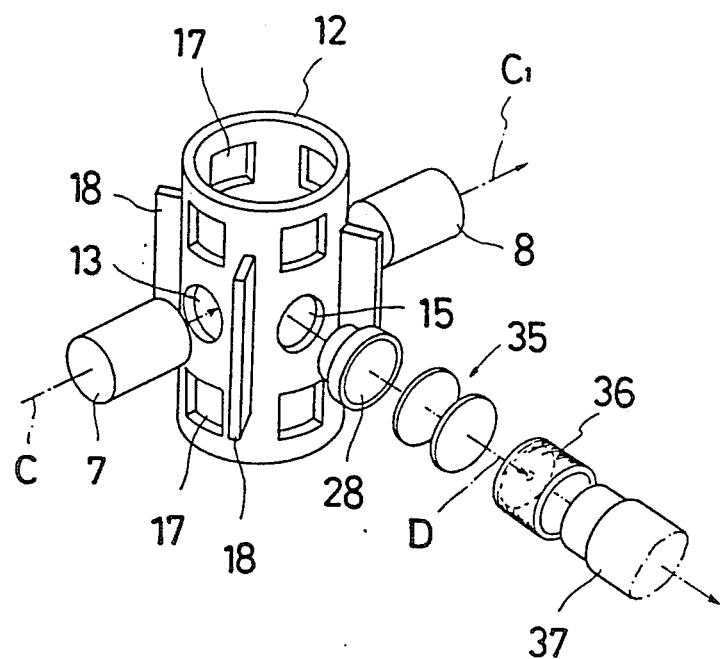
FIG. 5 is a perspective view of a rectifying cylinder partly in section and in which a fitting member is slightly separated from an optical fiber.
Figure 6:
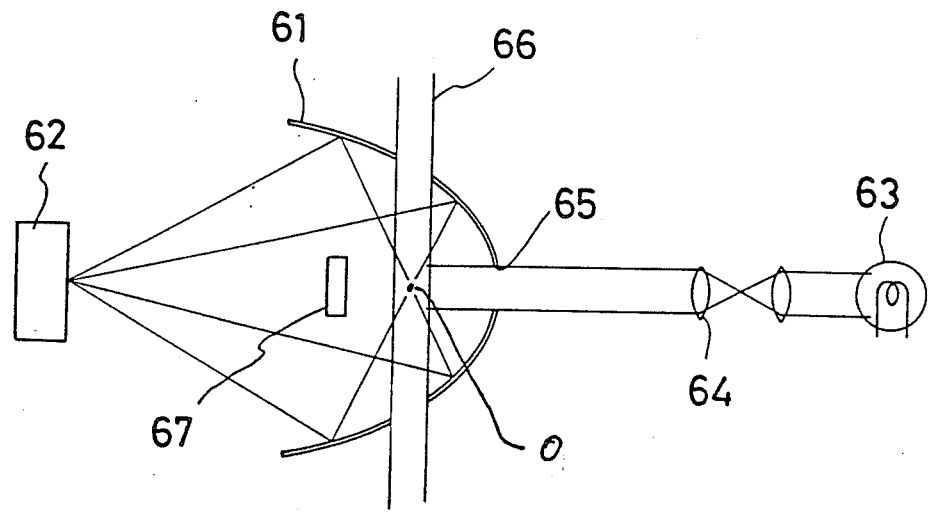
FIG. 6 is a schematic view showing a conventional measuring apparatus.

In the measurement of particles contained in liquid by means of the above described apparatus, a sheath flow liquid B having the same index of refraction as the sample liquid, such as superpure water filtered by means of a filter, is supplied to the cell 1 through the supply pipe 25 and then passes through the cell 1 and inside of the rectifying cylinder 12 and is discharged through the drainage pipe 26 (refer to FIG. 4). Sample liquid, such as water fed through the supply pipe 19 is discharged into the sheath liquid in the rectifying cylinder 12 through the nozzle 20 at a pressure higher than that of the sheath liquid. The sample liquid discharged into the sheath liquid goes straight through the sheath flow liquid without being mixed with the sheath liquid for a certain distance above the nozzle 20 due to the difference in pressure, and then is mixed with the sheath liquid and discharged together therewith. That is to say, the sample liquid flows in a straight laminar stream in which it is surrounded by the sheath liquid after it is discharged from the nozzle 20. The incident light beam C from light source 24, such as a He-Ne laser, passes through the transmitting body 7 and the opening 13 and reach the sample flowing straight in the laminar relation to the sheath liquid and the passed through beam of light $C_1$, which has passed through the sample liquid, passes through the transmitting body 8. Accordingly, if particles are contained in the sample liquid, the incident beam C collides with said particles and light is scattered, as shown in FIG. 4 within the circled portion A, and a part of the scattered light is incident upon the optical fiber 37 through the opening 15, the transmitting body 28, the optical system 35 and the pin hole 38 (refer to FIG. 5) The number times light is incident upon the optical fiber 37 is counted by the optical detector 40, whereby the amount of particles contained in a unit volume of water is measured.

With this measuring apparatus, since the incident beam C is incident upon the sample liquid flowing straight in a laminar form in the sheath liquid, said incident beam C can go straight to the sample liquid through the sheath liquid and no scattering of light due to a difference in refractive index is produced, so that a measurement of high accuracy can be achieved. Since the rectifying cylinder 12 has a relatively small diameter, the sheath liquid gently flows through the inside of the rectifying cylinder 12, so that it is easy to obtain a laminar flow of the sample liquid.

In the above described embodiment, since the sleeve 36 for holding the optical fiber 37 is adjustably mounted in the support cylinder 34 by means of the set screw 39, it is easy to position the optical fiber 37 at a focus of the optical system 35. Further, since the optical detector 40 can be spaced from the body of the measuring apparatus, in which liquid is used, if the optical detector 40 is connected to the support cylinder 34 through the optical fiber 37 in the above described manner, the optical detector 40 is easy to maintain and control. An electric detector can be isolated from a liquid handling device. It is possible also to mount the optical detector 40 at a position opposed the optical system 35 without using the optical fiber 37.

Also, although air bubbles due to the flow of the sheath liquid can be prevented from being generating by causing the end portions of the transmitting bodies 7, 8 and 28 to project into the cell 1, the transmitting bodies 7, 8 and 28 may be optionally arranged. For example, they may be positioned flush with the internal surface of the cell 1. Although the liquid passage holes 17 are shown as spaced from the end portion of the rectifying cylinder 12, they may be formed by cutting the end edge of the rectifying cylinder 12.

Also, although the transmitting bodies 7, 8 and 28 are disclosed as being formed of silica glass and a He-Ne laser is disclosed as being used as the incident light in the above embodiment, the transmitting bodies 7, 8 and 28 may be formed of any materials suitable for the transmission of light rays can be used and an optional incident light beam can be used. Further, the rectifying cylinder 12 may be provided with a rib (not shown) formed on the internal surface thereof parallel to the axis thereof.

In addition, although in the above described example a sample liquid, from which minute particles were removed by means of a filter, was used as a sheath flow liquid, a super pure water prepared apart from such a sample liquid may be used. In addition, in the case where the sample liquid is the super pure water whose low-concentration minute particles are to be measured, such a superpure water may safely be used as the sheath flow liquid as it is without filtering.

As described above, according to the present invention, since incident light passes through a sample liquid flowing in a sheath around the sample liquid, which is flowing in a straight path in a rectifying cylinder at a pressure higher than that of the sheath liquid, said incident light goes straight from the sheath liquid to the sample liquid, so that there is no possibility that scattered light due to a difference in refractive index is produced, whereby particles in the sample liquid can be detected with high accuracy.

Also, it is possible to make the rectifying cylinder polygonal in cross-section so as to make the internal surface of the rectifying cylinder flat. As a result, the sheath flow liquid can flow gently so as not to produce a turbulent flow therein, whereby it is easy to obtain a laminar flow of the sample liquid. In addition, since the rectifying cylinder is provided with partition walls on outside thereof, scattered light can be prevented from reaching the transmitting portion transmitting light from detected particles even if a part of incident light, which passed through the transmitting portion of the cell, is scattered, whereby the measurement can be carried out with higher accuracy.

What is claimed is:

1. An apparatus for measuring particles contained in a sample liquid, comprising:
    a cylindrical cell having an incident light transmitting portion, a passed through light transmitting portion diametrically aligned with said incident light transmitting portion, and a scattered light transmitting portion at an angle to the diameter between said incident light transmitting portion and said passed through light transmitting portion;
    an inlet at one end of said cell for admitting sheath flow liquid having the same index of refraction as the sample liquid, and an outlet at the other end of said cell;
    a rectifying cylinder within said cell and having the axis extending between said inlet and said outlet and perpendicular to the diameter between said incident light transmitting portion and said passed through light transmitting portion and having light passing holes therein aligned with said incident light transmitting portion, said passed through light transmitting portion and said scattered light transmitting portion, said rectifying cylinder being coated with an opaque material, said cylinder being for causing said sheath flow liquid to flow smoothly from said inlet to said outlet at a predetermined pressure;
    a nozzle within said rectifying cylinder coaxial with the axis thereof and directed toward said outlet and upstream of said diameter and for discharging sample liquid into said cylinder at a pressure higher than said predetermined pressure;
    a plurality of partition walls on the outside of said cylinder between said incident light passing hole, said scattered light passing hole and said passed through light passing hole and extending parallel to the axis of said cylinder for guiding flow of sheath flow liquid along the outside of said cylinder; and
    an optical detector optically connected to said scattered light transmitting portion for detecting light scattered from particles in the sample liquid.

2. An apparatus as claimed in claim 1 in which the peripheral surfaces of said light transmitting portions are coated with an opaque material.

3. An apparatus as claimed in claim 1 in which said scattered light transmitting portions at right angles to said diameter.

4. An apparatus as claimed in claim 1 in which the opposite ends of said cylinder are mounted in the end walls of said cell, and said cylinder is spaced inwardly from the walls of said cell, and said cylinder has liquid passing holes in the end toward the inlet and the end toward the outlet causing the sheath flow liquid to flow along the outside of the cylinder and the inside of the cylinder.

* * * * *